(12) United States Patent
Knox et al.

(10) Patent No.: US 8,785,428 B2
(45) Date of Patent: Jul. 22, 2014

(54) VERMIN POISON

(75) Inventors: Richard J. Knox, Carmarthen (GB); Roger Melton, Carmarthen (GB); Philip Burke, Carmarthen (GB)

(73) Assignee: Morvus Technology Limited, Llanarthne, Carmarthen (GB)

( * ) Notice: Subject to any disclaimer, the term of this patent is extended or adjusted under 35 U.S.C. 154(b) by 1017 days.

(21) Appl. No.: 12/443,447

(22) PCT Filed: Sep. 28, 2007

(86) PCT No.: PCT/GB2007/003704
§ 371 (c)(1),
(2), (4) Date: Mar. 15, 2010

(87) PCT Pub. No.: WO2008/038023
PCT Pub. Date: Apr. 3, 2008

(65) Prior Publication Data
US 2010/0166871 A1   Jul. 1, 2010

(30) Foreign Application Priority Data
Sep. 30, 2006 (GB) .................................. 0619326.2

(51) Int. Cl.
*A01N 43/00* (2006.01)

(52) U.S. Cl.
USPC .......................................... 514/183; 514/579

(58) Field of Classification Search
USPC .................................................. 514/183, 579
See application file for complete search history.

(56) References Cited

U.S. PATENT DOCUMENTS

| | | |
|---|---|---|
| 3,208,999 A | 9/1965 | Jarowenko et al. |
| 4,251,536 A | 2/1981 | Johnson |
| 4,806,354 A * | 2/1989 | Green .......................... 424/687 |
| 4,950,306 A | 8/1990 | Marte et al. |
| 5,633,158 A | 5/1997 | Anlezark et al. |
| 5,780,585 A | 7/1998 | Anlezark et al. |
| 5,831,097 A | 11/1998 | Ebel et al. |
| 5,873,912 A | 2/1999 | Carlough |
| 5,977,065 A | 11/1999 | Anlezark et al. |
| 6,436,905 B1 * | 8/2002 | Tonge et al. .................... 514/23 |
| 2003/0228285 A1 | 12/2003 | Hung et al. |
| 2004/0053208 A1 | 3/2004 | Zavizion et al. |

FOREIGN PATENT DOCUMENTS

| | | |
|---|---|---|
| EP | 0 364 752 | 4/1990 |
| EP | 0 540 263 | 5/1993 |
| EP | 0 638 123 | 2/1995 |
| GB | 2035803 | 6/1980 |
| GB | 2365338 | 2/2002 |
| JP | 52-145523 | 12/1977 |
| RU | 2 078 502 | 5/1997 |
| WO | WO-88/07378 | 10/1988 |
| WO | WO-93/08288 | 4/1993 |
| WO | WO-95/35100 | 12/1995 |
| WO | WO-96/03151 | 2/1996 |
| WO | WO-97/23456 | 7/1997 |
| WO | WO-98/35701 | 8/1998 |
| WO | WO-98/52547 | 11/1998 |
| WO | WO-99/32113 | 7/1999 |
| WO | WO-99/61409 | 12/1999 |
| WO | WO-00/10611 | 3/2000 |
| WO | WO-01/64739 | 9/2001 |
| WO | WO-2004/035769 | 4/2004 |
| WO | WO-2005/002570 | 1/2005 |
| WO | WO-2005/067404 A2 * | 7/2005 |
| WO | WO-2006/003492 | 1/2006 |
| WO | WO-2007/026166 | 3/2007 |
| WO | WO-98/57662 | 12/2008 |

OTHER PUBLICATIONS

Bodmeier, Encapsulation of lipophilic drugs within enteric microparticles by a novel coacervation method, Jul. 15, 2006, International Journal of Pharmaceuticals, vol. 326, pp. 128-138.*
Adams et al., J. Nat'l. Cancer Inst. (1980) 64:555-560.
Anlezark et al., Biochem. Pharmacol. (1992) 44:2289-2295.
Conners et al., Int. J. Cancer (1971) 7:86-92.
Friedlos et al., Biochem. Pharmacol. (1992) 43:1249-1254.
Knox et al., Methods Enzymol. (2004) 382:194-221.
Knox et al., Cancer Res. (1986) 46:1972-1979.
Knox et al., Biochem. Pharmacol. (1992) 44:2297-2301.
Knox et al., Cancer Res. (2000) 60:4179-4186.
Knox et al., Biochim. Biophys. Acta (1987) 908:214-223.
Knox et al., Mutat. Res. (1991) 255:227-240.
Li et al., Bioorg. Med. Chem. (2003) 11:4171-4178.
Malisza et al., Arch. Biochem. Biophys. (1995) 316:680-688.
Skelly et al., Mini Rev. Med. Chem. (2001) 1:293-306.
Workman et al., Cancer Chemother. Pharmacol. (1986) 16:9-14.
Wu et al., Arch. Biochem. Biophys. (1997) 347:221-228.
Aghi et al., J. Gene Med. (2000) 2:148-164.
Anlezark et al., Biochem. Pharmacol. (1995) 50:609-618.

(Continued)

*Primary Examiner* — Ali Soroush
(74) *Attorney, Agent, or Firm* — Morrison & Foerster LLP

(57) ABSTRACT

Use of an orally or nasally available formulation of Tretazicar for poisoning vermin. An orally available or nasally available formulation of Tretazicar, wherein in the orally available formulation the Tretazicar is protected from acid hydrolysis, and provided that the formulation is not solid Tretazicar in a gelatin capsule. A formulation of Tretazicar in which the Tretazicar is protected from acid hydrolysis, wherein the formulation is present in a liquid form. A combination of Tretazicar and bait. A method of poisoning vermin comprising making available to the vermin an orally or nasally available formulation of Tretazicar and allowing the vermin to ingest or inhale the formulation of Tretazicar.

21 Claims, No Drawings

(56) References Cited

OTHER PUBLICATIONS

Apple et al., Cancer Chemother. Report (1968) 52(7):687-696.
Bailey et al., Gene Ther. (1996) 3:1143-1150.
Buckner et al., Antimicrobial Agents and Chemotherapy (1996) 40(11):2592-2597.
CAPLUS abstract No. 1966:68533 (Ilg et al., Textil-Praxis 1965 20(11):916-920) (English abstract only).
CAPLUS abstract No. 1967:17926 (Von Ardenne, Naturwissenschaften 1964 51:217-218) English abstract only).
Collins et al., Clinical Cancer Research (1999) 5:1976-1981.
Croft and Yardley, Animal Models of Visceral Leishmaniasis, in Handbook of Animal Models of Infection, Zak, O. (ed.), pp. 783-787 (1999), Academic Press London.
Gutierrez, Frontiers in Bioscience (2000) 5:d629-638.
Hauge et al., J. Biol. Chem. (1955) 214:11-26.
Heller et al., Bulletin de l'Academie Polonaise des Sciences (1968) 16(7):401-405.
Hu et al., J. Med. Chem. (2003) 46:4818-4821.
Kammerer et al., In Vivo (2004) 18(6):795-798.
Knox et al., Biochem. Pharmacol. (1988) 37:4671-4677.
Loadman et al., Biochem. Pharmacol. (2000) 59:831-837.
Mauger et al., J. Med. Chem. (1994) 37:3452-3458.
Murray et al., Antimicrob. Agents Chemother. (1993) 37:1504-1505.
Nelson, J. Biol. Chem. (1944) 153:375.
Neumuller, Rompps Chemie-Lexikon, 8$^{th}$ ed., (1981) p. 1513.
Pozas et al., Bioorg. Med. Chem. Letts. (2005) 15:1417-1421.
Rauth et al., International Journal of Radiation: Oncology Biophysics (1998) 42(4):755-762.
Smyth et al., J. Org. Chem. (1998) 63:7600-7618.
Wolkenberg, Tetrahedron Letters (2001) 1-5.
Venitt and Crofton-Sleigh, Mutagenesis (1987) 2:375-381.
Weedon et al., Int. J. Cancer (2000) 86:848-854.
Wei and Pei, Bioorg. Med. Chem. Lett. (2000) 10:1073-1076.
Woessner et al., Anticancer Research (2000) 20:2289-2296.
"International Nonproprietary Names for Pharmaceutical Substances (INN)" WHO Drug Information (2005) 19(2):161-198.
Boland et al., Biochem. Pharmacol. (1991) 41:867-875.
Bridgewater et al., Eur. J. Cancer (1995) 31A:2362-2370.
Bridgewater et al., Human Gene Therapy (1997) 8:709-717.
Chen et al., J. Biol. Chem. (1997) 272:1437-1439.
Chen et al., Mol. Pharmacol. (1995) 47:934-939.
Chung-Faye et al., Clin. Cancer Res. (2001) 7:2662-2668.
Cobb et al., Biochem. Pharmacol. (1969) 18:1519-1527.
Cobb, Toxicology and Applied Pharmacology (1970) 17:231-238.
Cui et al., Gene Ther. (1999) 6:764-770.
Cui et al., Glia (2001) 34:272-282.
Ernster, Chemica Scripta (1987) 27A:1-13.
Felmer et al., Journal of Endocrinology (2002) 175:487-498.
Friedlos et al., Gene Therapy (1998) 5:105-112.
International Search Report for PCT/GB2007/003704, mailed on Jan. 28, 2008, 3 pages.
International Preliminary Report on Patentability for PCT/GB2007/003704, issued on Mar. 31, 2009, 7 pages.
Isles et al., J. Neurobiol. (2001) 47:183-193.
Khan and Ross, Chem-Biol. Interactions (1969) 1:27-47.
Knox et al., Biochem. Pharmacol. (1988) 37:4661-4669.
Knox et al., Biochem. Pharmacol. (1991) 42:1691-1697.
Knox et al., Biochem. Pharmacol. (1993) 46:797-803.
Knox et al., Cancer and Metastasis Review (1993) 12:195-212.
Knox et al., Current Pharmaceutical Design (2003) 9:2091-2104.
Ma et al., Eur. J. Neurosci. (2002) 16:2317-2323.
Post et al., J. Cell Biol. (1963) 18:1-12.
Prochaska et al., J. Biol. Chem. (1986) 261:1372-1378.
Ross et al., Biochem. Pharmacol. (1969) 18:2683-2688.
Sheard et al., Br. J. Cancer (1971) 25:838-844.
Workman et al., Cancer Chemotherapy and Pharmacology (1986) 16:1-8.
Wu et al., Arch. Biochem. Biophys. (2001) 385:203-208.

* cited by examiner

VERMIN POISON

CROSS-REFERENCE TO RELATED APPLICATIONS

This application is the national phase of PCT application PCT/GB2007/003704 having an international filing date of 28 Sep. 2007, which claims priority from European application GB 0619326.2 filed 30 Sep. 2006. The contents of these documents are incorporated herein by reference.

The invention relates to a method for selectively poisoning vermin such as rodents, particularly rats.

The listing or discussion of a prior-published document in this specification should not necessarily be taken as an acknowledgement that the document is part of the state of the art or is common general knowledge.

Vermin such as rats are a problem throughout the world. For example, it has been estimated that 10% of the world's food supply is consumed or damaged by rats. The rat population in the United Kingdom is estimated at about 60 million, which is approximately the same as its human population. There has been a significant increase in the brown rat (*Rattus norvegicus*) population in the UK, particularly in the Home Counties region. The decay of and lack of maintenance funding for an ageing sewerage system, the use of plastic building products, the proliferation of fast food outlets, increasing urban litter, poor hygiene, reduction of local authority pest control funding, and resistance to first and second generation poisons may be contributing to the increase in population.

The rat population has become more resistant to many of the known poisons. Furthermore, the known poisons are typically toxic to other species such as humans, pets, other mammals and birds. For example, red kites are a protected species and subject to an ongoing restoration programme. The population of red kites could be at risk by scavenging on rats killed by rat poison. In this regard, poison residues have been found in kites.

The predominant vermin (particularly rat) poison products on the market remain the first generation anti-coagulant warfarin and its analogues, and second generation anti-coagulants such as bromadiolone. The first generation anti-coagulants typically suffer from the development of resistance by rats and other vermin. The second generation anti-coagulants, although typically less prone to the development of resistance, are extremely toxic to a wide range of other species.

Rats are difficult to kill with poisons because their feeding habits reflect their place as scavengers. It is known that rats will initially avoid new foods and the initial sampling when bait is first taken is very small. If adverse effects occur rapidly thereafter, the bait will not be taken again, a situation known as bait-shyness. Thus an effective rat poison will typically be slow acting. In other words, symptoms will be slow to set in so that the rodent will continue eating the bait, thus avoiding bait-shyness. Other desirable characteristics of rat poisons are described below.

The poison should be palatable to vermin and should be toxic to vermin in an average quantity of consumed bait. Moreover, the vermin should not develop immunity or physical tolerance to the poison.

Ideally, the poison should be specific to a particular species or group of species, eg rats. The age and sex of the target species should not affect its susceptibility. The poison should present a minimal hazard to humans and other creatures such as domestic animals. There should also be a minimal risk of secondary poisoning of scavengers.

Ideally, the poison should be inexpensive to produce and easily formulated into solid and/or liquid bait. The poison should preferably degrade into harmless products.

The compound Tretazicar is 5-(aziridin-1-yl)-2,4-dinitrobenzarnide (CB1954), whose structure is shown below.

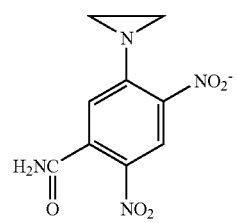

Tretazicar has the registry number C.A.S. No 21919-05-1 and its synthesis and use as an anticancer agent has been described in Khan & Ross, "Tumour growth inhibitory nitrophenylaziridines and related compounds: structure-activity relationships", *Chem-Biol Interactions* 1, 27-47 and in Cobb et al (1969) *Biochem. Pharmacol.* 18, 1519-1527.

Tretazicar is capable of eradicating a specific rat tumour ('Walker tumour'), though has little or no effect upon a variety of other tumours (Cobb et al (1969) *Biochem. Pharmacol.* 18, 1519-1527) and shows no therapeutic benefit in human clinical oncology studies (Knox et al (1993) *Cancer and Metastasis Rev.* 12, 195-212). It has been shown that a nitroreductase enzyme present in the Walker tumour is capable of activating Tretazicar by reducing its 4-nitro group to form the compound 5-aziridino-4-hydroxylamino-2-nitrobenzamine, a potent electrophilic DNA cross-linking agent in the presence of intracellular thioesters (Knox et al (1988) *Biochem. Pharmacol.* 37, 4661-4669; Knox et al (1991) *Biochem. Pharmacol.* 42, 1691-1697). The corresponding enzyme in human cells has relatively slow kinetics of reduction, thus rendering human cells insensitive to the effects of CB1954 (Boland et al (1991) *Biochem. Pharmacol.* 41, 867-875).

In addition to its potent and specific anti-tumour activity, Tretazicar has been shown to be toxic to rats (Cobb (1970) *Toxicol. Appl. Pharmacol.* 17, 231-238). However, Cobb considered it necessary to administer Tretazicar directly into the duodenum (or by other routes such as subcutaneously, intravenously and intraperitoneally) rather than orally because exposure of Tretazicar to the acidity of the stomach would cause it to be inactivated (Cobb (1970) *Toxicol. Appl. Pharmacol.* 17, 231-238). Workman et al showed that, when packed into a gelatin capsule, the oral bioavailability of Tretazicar in dogs was about 40% (Workman et al (1986) *Cancer Chemother. Pharmacol.* 16, 1-8) but did not propose an oral formulation of tretazicar for anti-tumour use.

The present inventors have now found that, surprisingly, the compound Tretazicar can be used as an orally available or nasally available poison for vermin, the poison having many, if not all, of the desirable features described above in relation to a rat poison. This is surprising considering that Tretazicar has been known for over 35 years and considered to be unsuitable for administration via the oral route.

The present invention provides the use of an orally or nasally available formulation of Tretazicar for poisoning vermin.

By the phrase "orally available" we include the meaning that the formulation is ingestible by vermin. In other words, the formulation is intended to enter or be taken by the vermin via the oral route, ie by eating or drinking. The formulation is one which is effective to poison the vermin when ingested by the vermin (and if sufficient is ingested it will kill the vermin). The formulation also typically allows Tretazicar to render its cytotoxic effect in the vermin when ingested or taken by the vermin. The orally available formulation containing Tretazicar is protected from acid hydrolysis, for example protected from the acid of the stomach.

Typically, orally available formulations are ones which withstand the acid in the stomach of the vermin and deliver Tretazicar to parts of the gastrointestinal tract beyond the stomach (such as the intestines, particularly the duodenum) in a form that can be absorbed and have its cytotoxic effect.

The invention includes use of Tretazicar for poisoning vermin wherein the Tretazicar is taken by the vermin by the oral route. The Tretazicar in this aspect of the invention is orally available.

By the phrase "nasally available" we include the meaning that the formulation is inhaled by vermin or absorbable by vermin across their nasal mucosa or membrane involved in gaseous exchange in the vermin. By way of example, it may be convenient to poison vermin which live in a nest by inhalation of a formulation of Tretazicar. Thus, the vermin may be poisoned (e.g. gassed) by Tretazicar in an aerosol formulation.

By "poisoning", we include the meaning that the Tretazicar impairs function, causes structural damage or otherwise injures the vermin, with the intent to kill the vermin. Preferably, the vermin are killed by the use, formulation, combination (e.g. composition) and method of the present invention.

By the term "vermin", we mean animals, particularly small animals, that are troublesome to man. For example, vermin includes rodents (particularly rats), birds (eg pigeons) and small mammals (eg moles, rabbits and squirrels), species of bandicoot, species of mastomys and ectoparasites (eg fleas, ticks, lice and mites).

The present invention provides a formulation of Tretazicar in which the Tretazicar is protected from acid hydrolysis and wherein the formulation is present in a liquid form.

The present invention also provides an orally available or nasally available formulation of Tretazicar, wherein in the orally available formulation the Tretazicar is protected from acid hydrolysis, and provided that the formulation is not solid Tretazicar in a gelatin capsule. For the avoidance of doubt, a gelatin capsule is not a microcapsule which, as discussed below, is included in the invention.

The aziridine ring of Tretazicar is known to be susceptible to acid hydrolysis (see, for example, Workman et al referenced above). Therefore, it has previously been considered unsuitable to administer Tretazicar orally because the acidic environment of the stomach is thought to hydrolyse the aziridine ring. The ring opened hydrolysis product does not have the toxicity towards vermin of Tretazicar (Khan & Ross, Chem Biol Interact, 1, 27-47(1969)).

The compositions or formulations of the invention preferably contain Tretazicar in a form that protects it from acid hydrolysis. In particular, the compositions or formulations of the invention preferably contain Tretazicar in a form that protects it from hydrolysis at a pH of from 1 to 7, for example from 1 to 4, more preferably 1 to 3 (eg 1 to 2) and at a temperature of 37° C. for at least 1 hour. Thus, Tretazicar may be protected from the acidic conditions found in the stomach of vermin. For example, the pH inside the stomach of rats is thought to be from 1.9 to 3 and the Tretazicar may be protected from acid hydrolysis over this pH range.

Protecting the Tretazicar from acid hydrolysis may be achieved, for example, by coating or encapsulating the Tretazicar. In this way, release of the Tretazicar under the acidic conditions found in the stomachs of vermin may be prevented. For example, the Tretazicar may be encapsulated in microcapsules comprising a component selected from gelatin, starch, waxes, cellulose acetate phthalate, polyvinyl acetate phthalate, methacrylic acid copolymers and mixtures thereof. However, as mentioned above, the formulations of the invention do not include solid Tretazicar in a gelatin capsule.

The term "starch" is used to include modified starches (eg cellulose as a modified starch) and starch derivatives such as ethers and esters of the parent compound. The starches used are preferably of food or pharmaceutical quality.

By the term "microcapsules", we mean microspheres or microparticles encapsulating the Tretazicar which are substantially spherical and of "micron ($\mu m$)" size. Conveniently, the microcapsules containing Tretazicar are present as a suspension or slurry in a liquid or as a solid It will be appreciated that while it is desirable to protect the Tretazicar from acid hydrolysis which may otherwise be caused by the conditions in the stomach of the vermin, it is also desirable that upon entry into the intestines, particularly the duodenum, that the Tretazicar is available so that it may exert its cytotoxic effect in the vermin and poison them. Thus, in a particularly preferred embodiment, any coating (eg encapsulating agent) which protects the Tretazicar from the acid conditions of the stomach is removed by the conditions found in the intestines where the pH is typically near 7 (eg from about 6 to 8 or 6.5 to 7.5). Polymeric materials, such as cellulose phthalate (eg hydroxypropyl methylcellulose phthalate) and/or hydroxypropyl methylcellulose acetate succinate, are available that may act as a coating or encapsulating agent for Tretazicar that withstand the acid conditions of the stomach but that disintegrate under the conditions found in the intestine eg duodenum. Conveniently, therefore, the Tretazicar is in a formulation which resists acid hydrolysis in the stomach but which releases the Tretazicar in the intestines, eg the duodenum. The Tretazicar in the formulation may be present in a solid form or in a liquid form (ie in solution). It is preferred that the Tretazicar in the formulation is present in a solid form (e.g. as a powder).

As mentioned above, rats are particularly troublesome vermin. The present inventors have surprisingly found that Tretazicar is especially suited for poisoning rats for a number of reasons. For example, Tretazicar is particularly toxic towards rats compared to other rodents. It has been reported that the $LD_{50}$ of Tretazicar in the rat is 28 mg/kg when administered intraperintoneally but 220 mg/kg in the mouse (Sheard et al (1971) *Br. J. Cancer* 25, 838-844). Moreover, the present inventors have surprisingly found that the toxic effects of Tretazicar in rats are delayed when administered via the oral route. This feature is believed to help prevent bait-shyness.

The present invention provides a combination of Tretazicar and bait.

By the term "bait", we mean a means for attracting, tempting or enticing. vermin. The bait may attract, tempt or entice the vermin using taste, scent, shape, colour or other means. For example, a device may be used to attract the vermin using its colour or shape. Preferably, however, the bait attracts, tempts or entices the vermin by taste and/or scent. The combination of the invention may be inhalable or ingestible, and is preferably a composition which is ingestible by vermin, especially rodents such as rats. Accordingly, the bait is preferably a foodstuff and the composition preferably comprises Tretazicar and a foodstuff.

The foodstuff can be any material or substance that can be used as food. Thus, the bait may simply be a liquid for attracting the vermin by taste and/or scent. The term foodstuff does not include water itself, but aqueous or oil solutions of other foodstuffs are included, such as sugar solutions. In one preferred embodiment, the bait does not consist essentially of peanut oil or a mixture of peanut oil (also known as arachis oil) and acetone. In other words, the combination of the invention preferably does not contain only Tretazicar and peanut oil or only Tretazicar and peanut oil and acetone.

Preferably, the foodstuff is a solid foodstuff selected from cereals, meat, dairy produce, fruit, vegetable, beans, pulses and nuts. Preferably, the foodstuff comprises a cereal such as wheat, oatmeal, barley, rye, rice, maize or millet.

It is envisaged that the formulations of the invention described earlier herein could be mixed with bait. For example, the compositions and orally available formulations of the invention preferably comprise a solution of Tretazicar mixed with bait. This enables more thorough and even mixing of Tretazicar with the bait and can help to mask the taste or smell of the Tretazicar, thus avoiding bait-shyness.

For example, a solution of Tretazicar in an oil may be mixed with the solid bait (eg a solid foodstuff). The oil is typically edible and may have a taste or scent that helps to mask the taste or scent of the Tretazicar. A preferred oil is peanut oil. Another preferred oil is vegetable oil.

Other embodiments include the combination of an orally available formulation of Tretazicar (such as an encapsulated form which resists acid hydrolysis in the stomach but which is released in the intestines) and a device attractive to vermin or a foodstuff, particularly a solid foodstuff. Conveniently, the orally available formulation of Tretazicar is supplied to the person wishing to poison vermin in a form for addition to a vermin-attractive device or a foodstuff, with instructions for its use in poisoning vermin. Conveniently, the vermin-attractive device or the foodstuff may also be supplied, either together with, or separate from the orally available formulation of Tretazicar.

Like the formulations of the invention described earlier herein, the compositions preferably protect the Tretazicar from acid hydrolysis. Thus, the Tretazicar may be protected from hydrolysis by the acidic conditions found in the stomach of vermin. In other words, the compositions are adapted to resist release of the Tretazicar until it reaches the intestine (eg the duodenum) of the vermin. This may be achieved, for example, by coating or encapsulating the Tretazicar as described earlier herein.

The present invention also provides a method of poisoning vermin comprising making available to the vermin an orally or nasally available formulation of Tretazicar and allowing the vermin to ingest or inhale the formulation of Tretazicar.

Preferably, the Tretazicar formulation is provided at a site or location frequented by vermin, such as basements, drains and sewers.

The amount of Tretazicar in the orally available formulation is ideally sufficient to poison the vermin which frequent the site where the formulation is made available. However, it is sometimes difficult to ascertain the number of vermin which frequent a site. In any case, the amount of Tretazicar made available is preferably sufficient to poison (preferably to kill) at least one rodent when ingested. More preferably, the amount of Tretazicar made available is preferably sufficient to poison (preferably to kill) at least one rat. Conveniently, the amount of Tretazicar made available to the vermin is sufficient to poison (preferably to kill) at least 5, preferably at least 10 and more preferably at least 20 vermin. It will be appreciated that because of the feeding habits of vermin, particularly rats, that the vermin may not take (ingest) sufficient Tretazicar to kill them in one go; rather repeated ingestion may be required to deliver the lethal dose. Thus, the vermin are encouraged to return to the site where the Tretazicar has been placed and/or more than one site or location of the vermin has Tretazicar made available to the vermin.

Typically, at least 500 mg of Tretazicar mixed with bait is made available at a single site. Of course, this amount will vary depending on the number and size of vermin considered to frequent the site and/or the number of vermin that it is desirable to poison. On this basis it is possible to calculate the amount of Tretazicar that should be sufficient to poison or kill a given number of rats. For example, hundreds, thousands or even more rats may frequent a sewer. In this case, as much as 200 g or even as much as 1 kg of Tretazicar might be made available at a single site.

The orally available formulation of Tretazicar for use in the method of the invention preferably comprises bait, as described above in relation to the compositions of the invention. More preferably, the formulation comprises bait mixed with a solution of Tretazicar, for example a peanut oil solution.

The formulations of Tretazicar used in the method of the present invention are preferably formulated so as to resist release of the Tretazicar until it reaches the intestine of the vermin. This is typically achieved by the methods described earlier herein, such as microencapsulation.

The invention claimed is:

1. A composition comprising Tretazicar and a bait wherein the bait comprises solid foodstuff selected from cereals, meat, dairy produce, fruit, vegetables, beans, pulses and nuts and combinations thereof, and wherein Tretazicar is the only cytotoxic ingredient in said composition.

2. The composition of claim 1 wherein the foodstuff comprises a cereal.

3. The composition of claim 2 wherein the cereal is wheat, oatmeal, barley, rye, rice, maize or millet.

4. The composition of claim 1 comprising a solution of Tretazicar in said bait which is an oil mixed with the solid foodstuff.

5. The composition of claim 4 wherein the oil is peanut oil or vegetable oil.

6. The composition of claim 1 wherein the Tretazicar is protected from acid hydrolysis.

7. The composition of claim 1 which is adapted to resist release of the Tretazicar until it reaches the intestine of a rat, when ingested by the rat.

8. The composition of claim 7 wherein the Tretazicar is encapsulated in microcapsules.

9. The composition of claim 8 wherein the microcapsules comprise a component selected from gelatin, starch, waxes cellulose acetate phthalate, polyvinyl acetate phthalate, hydroxypropyl methylcellulose phthalate, hydroxypropyl methylcellulose acetate succinate, methacrylic acid copolymers and mixtures thereof.

10. A method of poisoning rats which comprises making available to the rat the composition of claim 1 and allowing the rats to ingest said composition.

11. The method of claim 10 wherein the said composition is provided at a site frequented by rats.

12. The method of claim 10 wherein the composition contains at least 100 mg of Tretazicar.

13. The method of claim 10 wherein the Tretazicar is protected from acid hydrolysis.

14. The method of claim 10 wherein the composition comprises a solution of Tretazicar mixed with the foodstuff.

15. The method of claim 10 wherein the composition comprises an oil solution of Tretazicar mixed with foodstuff.

16. The method of claim 15 wherein the oil is peanut oil or vegetable oil.

17. The method of claim 10 wherein the composition is formulated to resist release of the Tretazicar until it reaches the intestine of a rat, when ingested by the rat.

18. The method of claim 17 wherein the Tretazicar is encapsulated in microcapsules prior to mixing with the foodstuff.

19. The method of claim 18 wherein the microcapsules comprise a component selected from gelatin, starch, waxes cellulose acetate phthalate, polyvinyl acetate phthalate, hydroxypropyl methylcellulose phthalate, hydroxypropyl methylcellulose acetate succinate, methacrylic acid copolymers and mixtures thereof.

20. A kit of parts comprising the composition of claim 1 or Tretazicar and a vermin-attractive device wherein said attractive device is not a foodstuff.

21. The kit of parts of claim 20, wherein the Tretazicar is protected from acid hydrolysis.

* * * * *